(12) United States Patent
Tran

(10) Patent No.: US 7,029,855 B1
(45) Date of Patent: Apr. 18, 2006

(54) RADIOACTIVE MULTIPLEXING ANALYTICAL METHODS FOR BIOMARKERS DISCOVERY

(75) Inventor: Nathaniel Tue Tran, Irvine, CA (US)

(73) Assignee: Proteomyx Inc., Temecula, CA (US)

( * ) Notice: Subject to any disclaimer, the term of this patent is extended or adjusted under 35 U.S.C. 154(b) by 70 days.

(21) Appl. No.: 10/680,277

(22) Filed: Oct. 7, 2003

Related U.S. Application Data (60) Provisional application No. 60/443,017, filed on Jan. 28, 2003.

(51) Int. Cl.
  *C12Q 1/68* (2006.01)
  *G01N 33/53* (2006.01)

(52) U.S. Cl. .......................... 435/6; 435/7.1
(58) Field of Classification Search .................. 435/6, 435/7.1; 530/350; 536/23.1, 24.3
See application file for complete search history.

(56) References Cited

U.S. PATENT DOCUMENTS

| | | | | |
|---|---|---|---|---|
| 4,016,250 A | * | 4/1977 | Saxena | 436/504 |
| 4,524,275 A | * | 6/1985 | Cottrell et al. | 250/298 |
| 4,628,205 A | | 12/1986 | van Cauter et al. | |
| 4,918,310 A | | 4/1990 | Rundt et al. | |
| 5,120,962 A | | 6/1992 | Rundt et al. | |
| 5,753,917 A | | 5/1998 | Engdahl | |
| 5,807,522 A | * | 9/1998 | Brown et al. | 422/50 |
| 6,203,993 B1 | * | 3/2001 | Shuber et al. | 435/6 |
| 2002/0006623 A1 | * | 1/2002 | Bradley et al. | 435/6 |
| 2003/0013126 A1 | * | 1/2003 | Singh et al. | 435/7.1 |
| 2003/0077840 A1 | | 4/2003 | Chait | |
| 2003/0162306 A1 | | 8/2003 | Dumas | |

FOREIGN PATENT DOCUMENTS

WO  WO0063701  * 10/2000

OTHER PUBLICATIONS

Ng et al. J. Cell. Mol. Med. 6 (3) : 329-340 (2002).*
Schena et al. Science 270 : 467-470 (1995).*
MacBeath G. Nature Genetics 32 : 526-532 (2002).*
Michaud et al. Biotechniques 33 (6) :1308-1316 (2002).*
Cutler P. Proteomics 3 : 3-18 (2003).*
H. Salin et. al. (2002) Nucleic Acids Research, vol. 30, No. 4 e17 A novel sensitive microarray approach for differential screening . . .

* cited by examiner

*Primary Examiner*—Ethan Whisenant (57) ABSTRACT

A novel analytical method involves labeling samples with different radioactive labeling agents, mixing and subjecting the mixture to any separation technique, and then differentially detecting and quantifying subcomponents from each sample for comparison. The novel technique exploits the differences in radiation energy or half-life between isotopes to make differential detection and quantification of labels possible. Detailed methods for differential detection and quantification are also described as well as the construction and application of hardware and software to enable and enhance such a process. This method is useful in finding molecular differences between two samples in differential proteomics, phosphor-proteomics, glycomics, metabolomics, transcriptomics, genomics and diagnostic applications.

17 Claims, 4 Drawing Sheets

RADIOACTIVE MULTIPLEXING ANALYTICAL METHODS FOR BIOMARKERS DISCOVERY

CROSS-REFERENCE TO RELATED APPLICATIONS

This application claims priority of provisional application U.S. Ser. No. 60/443,017, titled multiplexing analytical techniques, filed Jan. 28, 2003, the content of which is incorporated herein by reference.

BACKGROUND OF THE INVENTION

Many analytical methods require side-by-side or sequential comparison to quantitatively compare differences between two samples. For example, to compare proteins on a Western blot, samples are run on adjacent lanes; to compare small molecules on HPLC, samples are run sequentially one next to the others. This format of analysis requires twice the effort in sample preparation; in addition, variability can be introduced into the system if the treatments of one sample slightly deviated from another. For these reasons, many repetitions plus statistical analysis are required before any differences found become credible. A method that allows two samples to be mixed together for analysis and quantitative comparison will provide significant advantages in analytical precision.

Existing Methods:

Multiplexing methodologies have been around for a while especially the use of different color dyes for comparative labeling. For example, a tissue section can be used for simultaneous multiple immuno-histochemistry experiment by using antibody conjugated to different color dyes. The intensity of each dye is used to compare the relative abundance of each type of antigens that the different color-coded antibodies bind to.

Recently fluorescent dyes of different colors are used to label DNA, RNA, and even proteins to enable two or more of these samples to be mixed together and analyzed simultaneously. One application is a DNA array where DNA or RNA from different samples are labeled with dyes that fluoresce at two different wavelength, mixed, applied to the same array for competitive binding and then read to see which sample has more of which genes expressed. Another important application is the labeling of two proteins samples by different fluorescent colors dyes such as Cydyes sold by Amersham Biosciences and Alexa fluor dyes sold by Molecular Probes. These protein samples are then mixed and co-separated by 2-dimensional gel electrophoresis into thousands of dots based on the proteins' differences in isoelectric points and apparent molecular weights. A fluorescent scanner is used to read Cy2, Cy3 or Cy5 signal separately and computer software compare the signal intensity between them for quantitative comparison of protein abundance between the samples.

Labeling and Detection

The current labeling techniques for fluorescent labeling require coupling of bulky and disruptive fluorochromes to amino acids or nucleotides within the molecule of interest to facilitate detection. While DNA and RNA often can accommodate structural modifications caused by covalent linkage with dyes for DNA array analysis, proteins cannot for protein array analysis. A fluorochrome such as Cydye often will modify amino acids, such as lysine, and will effectively change the epitope structure that the lysine is involved in. As a result, the label interferes with the analyte and often prevents an antibody from binding normally to labeled proteins the same way it would to unlabeled proteins. Furthermore, dye may alter the structure of DNA or RNA significantly, such that proteins, e.g., transcription factors, won't be able to recognize and bind as they would do with native sequences.

Radioactive labeling solves the problem by making the labeling group much smaller, or better yet, by isotope replacement with identical atoms. Additionally, radioactive labeling is at least 100 times more sensitive than many other methods upon detection. Replacement labeling can be done with direct incorporation of labeled precursors such as amino acids yielding labeled proteins with absolutely no chemical modification. Such metabolic labeling techniques are done routinely in research laboratories. Once labeled, X-ray photography can be used to detect and record the respective radiation. Since X-ray film has a limited linear range thus usually not used for quantitative analysis, other methods have evolved over time. A commonly used method comprises the use of a phosphorescent storage imaging screen. The high-energy radiation excites the storage material's electrons into their phosphoresced state at which they will remain until excited again by the right quanta of energy. Using that principle, a phosphorescent screen captures some of the radiation energy, stores it, and gives back when read with a tuned laser. Such devices are also commonly used in photography. Another method that enables quantitative analysis of radiation is Scintillation Counting. A scintillation material is mixed with the radioactive sample so that when the material is struck with high-energy radiation it will give up light for easy detection and quantification. Direct detection with devices such as Geiger counter is also possible; however, the cost for making such instruments has limited its use.

SUMMARY OF THE INVENTION

The present invention discloses a method of analysis comprising the steps of: (1) labeling two samples of test molecules each with a unique radioactive labeling agent; (2) mixing the samples of test molecules into a homogenous mixture; (3) subjecting the mixture to means of analysis that separates the components in said mixture; and (4) reading the resulting radiation to determine the quantity of each component from each sample utilizing the difference in radiation energy or half-life.

This invention provides a novel method for coding individual samples, enabling the samples to be homogenized, testing the samples simultaneously and precisely the same way, then distinguishing and quantifying which molecules belong to which samples. One innovation is in the method that enables quantification of more than one isotope in a mixture. This is accomplished by exploiting the difference in radiation energy between isotopes or the difference in their half-life. By first quantifying total radiation and then quantifying partial radiation passing through a selective blocking screen, the amount of individual radiation from each isotope can be quantified knowing the efficiency of the screen in blocking different isotope. Alternatively, by quantifying total radiation, then storing the sample for radioactive decay (while preserving other attributes) before quantifying total radiation again, the amount of radiation between isotopes with different half-life can be selectively quantified. In addition to the time and cost savings by running two or more samples simultaneously, the increased reliability also provides new possibilities for analysis.

The main object of this invention is to provide an improved method for biomarker discovery. Generally two samples, whether drug treated compared against vehicle treated, or diseased compared against healthy, are labeled, mixed together, and separated by any number of means commonly known to one skilled in the art, into many fractions, bands, or dots. For example, molecules may be separated by chromatography, electrophoresis, immunoprecipitation, immunomagnetic capturing, array profiling, differential extraction or precipitation such as salt-cut precipitation or organic solvent extraction or precipitation, heat-treatment precipitation, microfluidic device, capillary electrophoresis, differential centrifugation, or gradient separation . . . etc. into many fractions or groups of molecules with less and less complexity.

The ratio of radioactive isotopes in each fraction can be easily monitored. Any fractions whose ratios deviate from a standard ratio can be examined further to identify the exact molecules in those fractions that are responsible. These are the molecules of interest because their levels of abundance vary between the test samples. The molecules can be identified by mass spectrometry and used as biomarkers for drug efficacy or diseased condition. Radioactive labeling with different isotopes also results in same molecules of different mass that can be differentiated and quantitatively compared during mass spectrometry analysis if necessary.

Another object of this invention is to provide a method for studying post-translational modifications. One set of sample is labeled with $^{32}P$ phosphates while the other set undergoing a different treatment is labeled with $^{33}P$ phosphates to study differential phosphorylation. Alternatively, one set of sample is labeled with $^{3}H$ sugar such as mannose while the other set is labeled with $^{14}C$ mannose for differential glycosylation studies. Phosphorylation or glycosylation samples can also be labeled with another isotope such as $^{35}S$ to determine the proportion of proteins that are modified. The two sets are mixed for analysis after labeling allows an unsurpassed degree of comparison. Other forms of post-translational modifications such as methylation, farnesylation, ubiquitination . . . etc. can also be studied by varying the types of labels use. These variations will be apparent to those skilled in the art.

A further object of this invention is to provide an improved method for genomic and proteomic analysis using radioactive isotopes of different radiant energy level or different half-life to enable simultaneous processing and quantification of multiple samples of DNA, RNA, proteins, and other molecules without damaging or rendering these molecules incomparable or incompatible for analysis purposes, e.g., chemically modifying them. Additionally and importantly, radioactive labeling also provides much higher sensitivity than any other methods of labeling.

A further object of the invention is the application of the technique toward comparing DNA methylation throughout the genome. One set of DNA can be methylated with $^{3}H$ donor groups while the other set methylated with $^{14}C$ donor groups. The DNA is then mixed together, digested into smaller fragments, and profiled onto a DNA array. Aberrations in signal ratios between the isotopes signify variations of the degree of methylation for particular captured genes.

DETAILED DESCRIPTION OF THE INVENTION

The invention provides a labeling and detection method for comparing profiles of a plurality of molecules derived from comparable sources. The method employs the use of radioactive isotopes which offer superior sensitivity for detection of any existing methods. In addition, radioactive isotopes can be incorporated directly into the molecules of interest eliminating any need for making any chemical modification to these molecules. To support the method, the invention also teaches ways to make supporting devices for increase performance of the method.

The first preferred embodiment is a method of quantifying different radioactive isotopes in a mixture. Scintillation counting allows differentiation between isotopes such as $^{3}H$ and $^{14}C$ because of the different light spectra that these isotopes generate. Tritium's radiation is relatively weak when compared to $^{14}C$'s. Thus tritium's scintillation pulse spectrum is not as broad as $^{14}C$'s allowing a multi-channel spectral analyzer to distinguish and quantify the ratio of these isotopes.

For multiple detections such as dots or bands on a gel, exposing to a phosphostorage screen and then read with a phosphoimager is a common way to quantify radiation. The present invention allows differential quantification by first exposing the gel to a phosphostorage screen for a fixed amount of time, then exposing again for the same duration with a blocking screen between the gel and the phosphostorage screen. Alternatively, both exposures can be taken simultaneously with double layer phosphostorage screen where the first layer also acts as a blocking screen.

Furthermore, both sides of the gels can be exposed simultaneously when possible. Blocking screens such as a layer of saran wrap block more than 95% of radiation from tritium while only block ~50% of radiation from $^{14}C$ or $^{35}S$. Similarly, an X-ray film can block more than 95% of radiation from $^{33}P$ but only blocks ~25% of radiation from $^{32}P$. Having standards of just individual isotope exposed with and without the blocking screen can allow one to calculate the percentage of signal passing through the screen at a certain isotope mixing ratio. Therefore the percentage of signal passing through the blocking screen can be used to determine the relative amount of individual isotope in the mixture.

The new labeling and detection technique enables many easier and more reliable approaches that can be used to look for changes in abundance of proteins or other molecules when these molecules are separated for analysis. A mixture of proteins from samples labeled with $^{3}H$ or $^{14}C$ respectively can be exposed to an antibody array for profiling specific proteins. Spots with antibodies specific for capturing housekeeping proteins are used as standards representing arbitrarily equal amounts of proteins in both samples. First, the average percentage of radiation blocked by a selective blocking screen from these spots is determined. Then, comparing this blocking percentage to the blocking percentage of other spots on the array is all that is needed to determine if there are any variations in abundance of captured proteins between the samples in the mixture. If a spot has lower blocking ratio (more radiation passing through the blocking screen), then the sample labeled with the stronger isotope $^{14}C$ possesses more proteins captured at that spot. If a spot has higher blocking ratio, then the sample labeled with weaker isotope $^3H$ has relatively more proteins captured at that spot. Because the proteins are structurally and chemically identical and they have competed fairly for binding to each of those antibody spots, we can infer that the samples have proportionally the same amount of proteins as captured on the array thus the samples can be accurately assessed and compared by this method.

Figure 1:
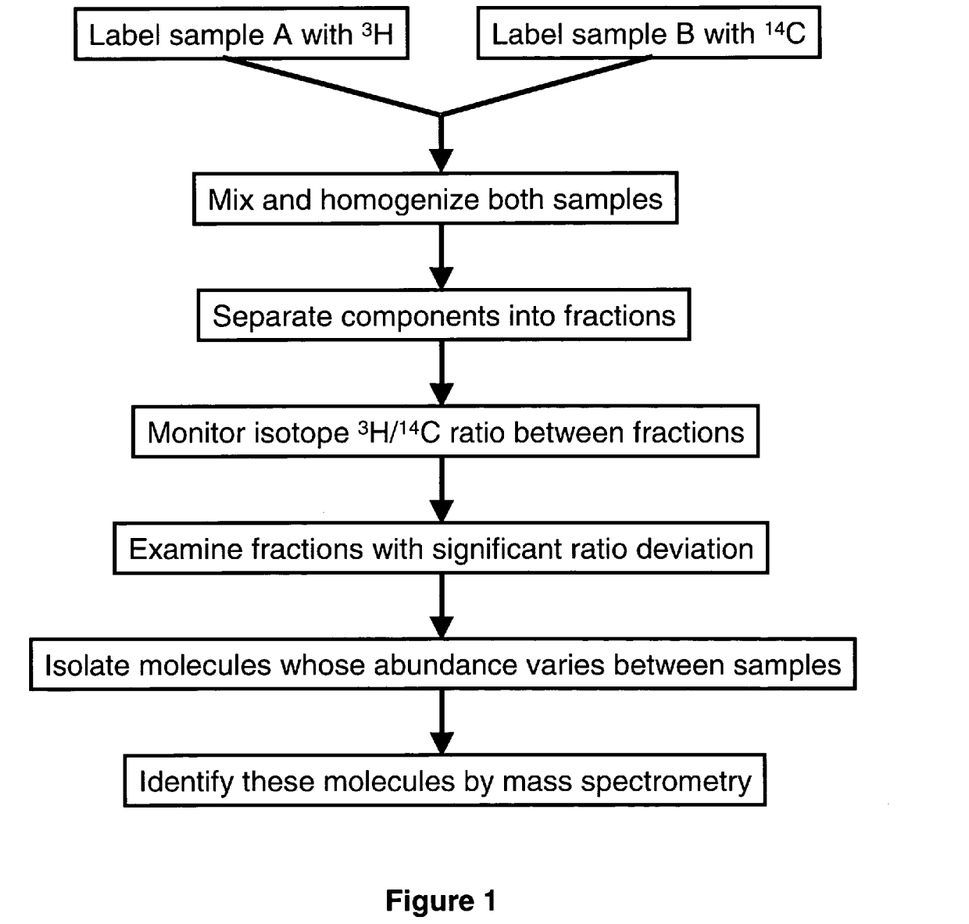
FIG. 1 is a flow-chart describing the biomarkers discovery process using different radioactive isotopes to encode molecules from two samples and the isotopes' differences in radiation energy to decode them after analysis.

With reference to FIG. 1, a second preferred embodiment comprises a method of discovering biomarkers and developing high-throughput assays using these biomarkers. Samples from treated and untreated cells labeled with different isotopes such as $^3H$ or $^{14}C$ are mixed together for analysis. The mixture is subjected to different types of chromatography one after another hereby refers to as tandem chromatography. The chromatography fractionates proteins based on their variations in size, charge, affinity to certain groups etc. . . . The fractions are continuously monitored to find any fraction with deviation in $^3H/^{14}C$ isotope ratio. The fractions with significant ratio deviation are further analyzed to single out the exact molecules responsible for the variation. These molecules are then identified by mass spectrometry. Then monoclonal antibodies against these molecules are made as component for an array for high-throughput screening. The array is used to capture and compare proteins from the original samples to validate the changes and the array itself. Then the array is ready to be used to screen for similar changes. For example, a working drug with known therapeutic efficacy can be used to produce biomarkers in a simple system such as a cell culture model. The discovered biomarkers are then used to make antibody arrays for high-throughput screening of other potential compounds with the same cell culture model to identify drug candidates with similar therapeutic efficacy.

A third preferred embodiment concerns methods that enable differential quantification of different isotopes in a mixture using the difference in their radiation energy. A blocking screen is used to selectively block higher proportion of radiation from the weaker isotopes while allowing higher proportion of radiation from the other isotope to pass. Alternatively, a scintillation material is used to convert radiation into light. Stronger radiation generate significantly broader spectrum of light thus can be differentiated from weaker radiation by a spectral analyzer. Detection and quantification may be achieved, for example by phosphor imaging or scintillation counting or more direct methods as used in Geiger counters. Different proportions of the two isotopes of interest can be used to establish a reference curve for accurate determination of isotope ratio in later experiment.

Figure 2:
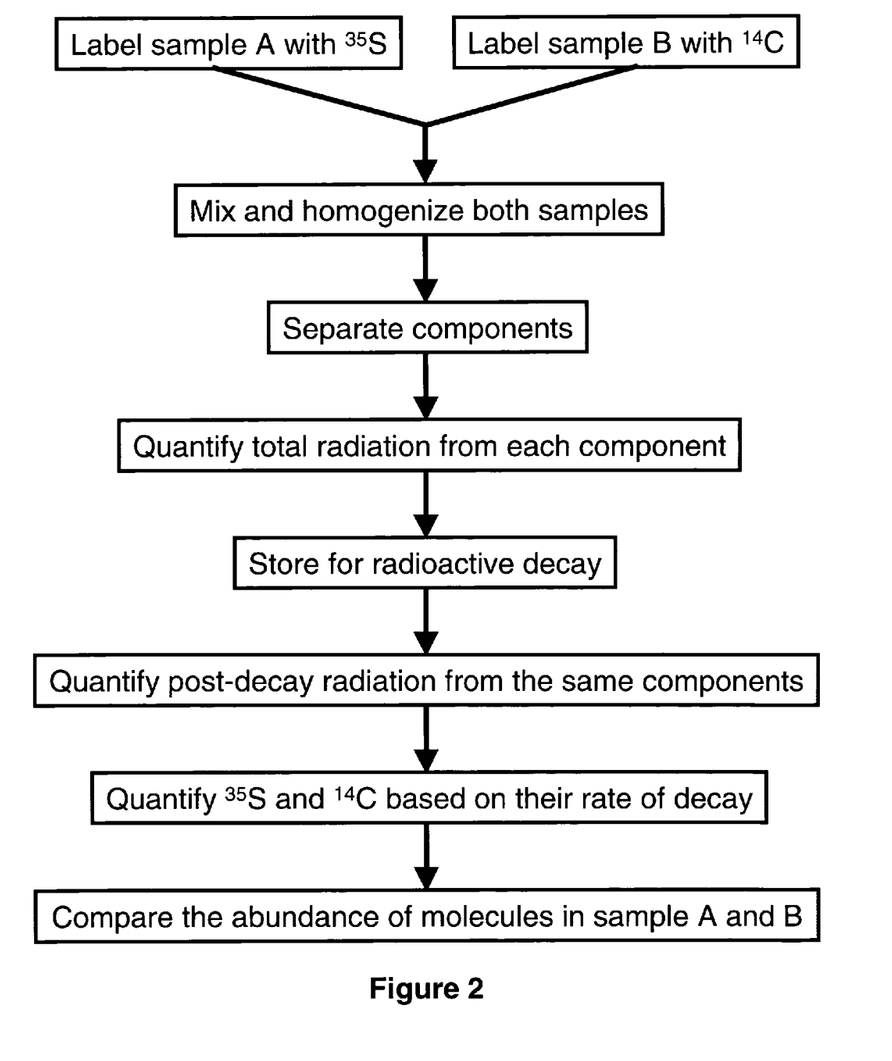
FIG. 2 is a flowchart describing an alternative biomarker discovering process using different radioactive isotopes to encode molecules from two samples and the isotopes' differences in half-life to decode them after analysis.

With reference to FIG. 2, illustrating a fourth preferred embodiment, mixtures containing at least two isotopes having significant differences in half-life are used for the purpose of quantitative analysis and comparison. This method of analysis can also be performed where the selective blocking method fails. An exemplary example is $^{14}C$ (156 keVmax) and $^{35}S$ (167 keVmax). When 14C and 35S are used together; a suitable method of analysis is used to quantify total radiation, then store for a decay period and then quantify total radiation again. The pre-decay and post-decay amounts of radiation read are used to calculate the amount of radiation unique to each isotope. This is possible because these two isotopes have different half-life: 5730 years for $^{14}C$ and 87.4 days for $^{35}S$. For simplicity, let's say the time period between the first quantification and the second quantification is 87.4 days which is exactly equal to one half-life of 35S. Then the signal difference between the first read and the second read must be equal to half the total $^{35}S$ signal from the first read. As a result signal unique to $^{35}S$ or $^{14}C$ can be calculated.

Figure 3:
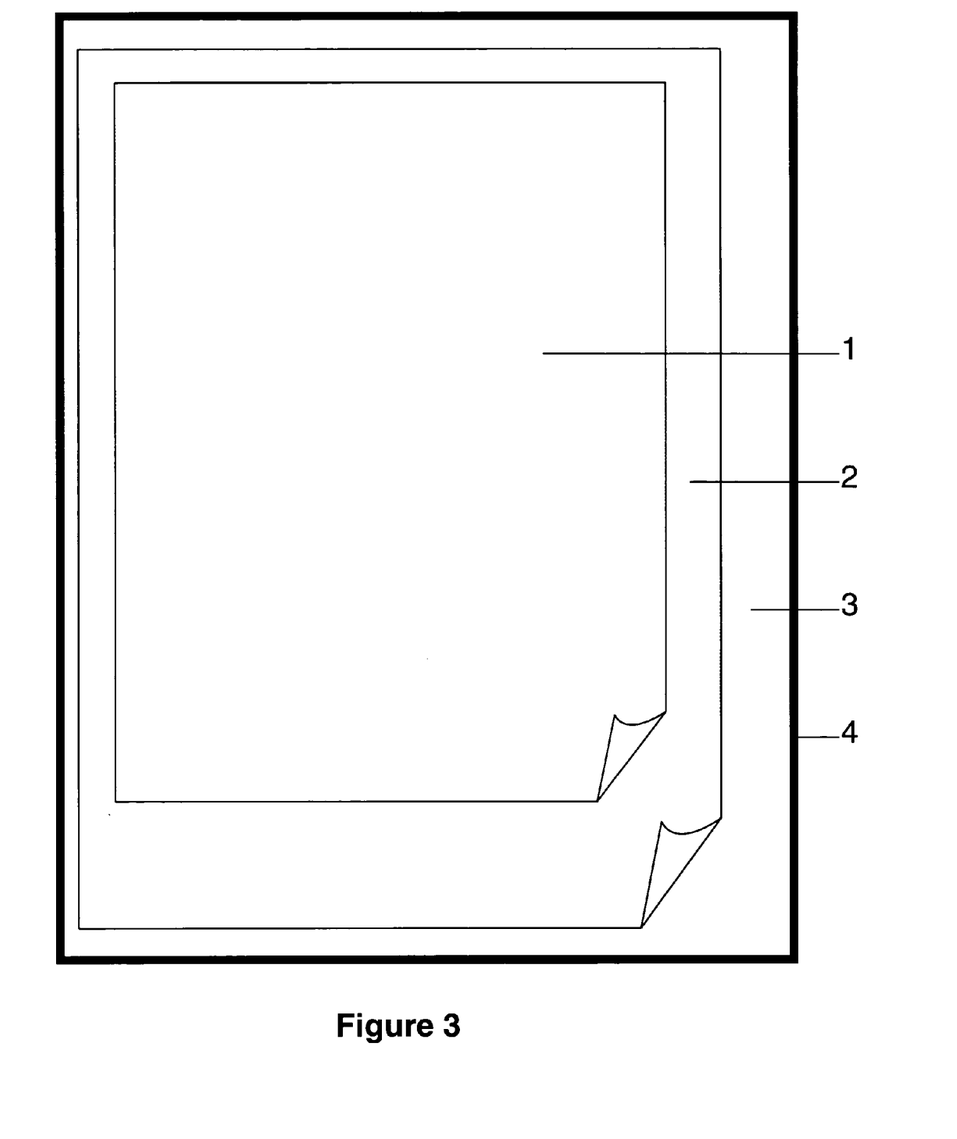
FIG. 3 is front view of a multi-screen phosphorescent storage and imaging system.

With reference to FIG. 3, the end result is usually a gel that can be dried onto a support material like a filter paper. The dried gel 1 is then exposed to a first phosphorescent imaging storage screen 2 and a second phosphorescent imaging storage screen 3. The screens would store the radiant energy so that it can only be released when excited by the right amount of energy. In addition the first screen 2 would serve the dual purpose of blocking weaker radiation signals so that the second screen 3 behind it only detects most of the radiation from the stronger isotopes. The screens 2 can be either a blocking screen or can also be a phosphorescent screen. The backing material 4 provides stability for the screens 2 and 3, but may support additional screens depending on the user's needs.

For blocking tritium, such screen 2 can be like a sheet of plastic saran wrap. For blocking $^{14}C$ and $^{35}S$, typical screens 2 construction requires the same blocking power as an X-ray film. Similarly, two X-ray films produce equivalent blocking for $^{33}P$, and 0.2 mm of lead or equivalent is sufficient to block most of $^{32}P$ signal while allowing 50% of the radiation from $^{125}I$ to pass. Such uniform screens along with complementary quantitative analysis software will enable the simultaneous detection and quantitative analysis of mixtures of multiple samples labeled with different radioactive isotopes. Additional screens can also be used to detect more isotopes simultaneously especially when radiation can also be detected from both sides of the gel or array.

In a fifth preferred embodiment of the invention, at least two samples can be analyzed and compared by labeling with radioactive isotopes of different energy level. The labeling may be done by covalent linkage like the one using NHS ester or by incorporation if the samples comprise live cells and are actively synthesizing the molecules of interest. Once labeling is completed, the two samples are mixed for analysis. For nucleic acids samples, the analysis can include but are not limited to gel electrophoresis, chromatography, and DNA array. For protein samples, analyses like protein array, SDS-PAGE, Immunoprecipitation, 2-d gel for proteomic analysis, various forms of chromatography including HPLC are preferred choices.

In a sixth preferred embodiment, the labeling of molecules with different radioactive isotopes is used to quantitatively compare subcomponents of molecules. These comprise certain characteristic of molecules such as the degree of phosphorylation of proteins or the degree of methylation of DNA. The degree of existing phosphorylation of proteins from two samples can be compared by further phosphorylating these proteins with $^{32}P$ or $^{33}P$ phosphates. The amount of labeled phosphates quantified on these proteins is thus indicative of how many phosphorylation sites are available. Such availability is indicative of preexisting degree of phosphorylation. Similarly, DNA methylation from two samples can be compared.

The above methods can also be combined in a seventh preferred embodiment to quantify isotopes' signal from a mixture of $^3H$, $^{14}C$ and $^{35}S$. The total radiation is first read and then the partial radiation passing through a screen is then read. The screen is designed to block proportionally higher percentage of radiation from tritium, thus tritium signal can be calculated from the first two read. Then the mixture, gel or array is stored for a significant amount of time relative to $^{35}$S's half-life. Then the sample is read again for total radiation. The reduction in signal is mostly due to $^{35}$S because even for 87 days, tritium with a half-life of ~12 years and $^{14}$C with a half-life of ~5730 years hardly decay at all. To improve reliability, dots of just $^3$H, $^{14}$C, and $^{35}$S should be added to the gel or array as internal standards to base the calculation on.

The use of specialized software can significantly automate the task minimizing operator errors. The user simply need to specify the standard dots representing single isotope of $^3$H, $^{14}$C, or $^{35}$S from all three exposures and the computer can do the rest. Even if exposure time may be inconsistent between the three times, there is enough data to perform the calculation to obtain the required signal reading for individual isotope. Alternatively, when standard dots are not available, the software can ask for exposure durations and decay time to perform the calculations necessary to obtain signal for individual isotope.

The most useful applications for this technique are for biomarkers discovery. Proteins can incorporate $^3$H and $^{14}$C labeled amino acids or even $^{35}$S when Cystein and Methionine are used for double-label or triple-label multiplexing analysis. In addition, multiple labels can be used for studying protein modifications, and interactions. Glycosylation can be differentially labeled with $^3$H or $^{14}$C glycan while proteins are labeled with $^{35}$S. Phosphorylation can also be compared with $^{32}$P and $^{33}$P while protein abundance is compared with $^3$H and $^{14}$C. The quadruple labeling also serves to determine which proportion of proteins is phosphorylated as well as comparing relative amount of phosphorylation and relative amount of protein expression all in one experiment.

Currently, radioactive Cystein and Methionine are only available commercially with $^{35}$S label while other amino acids are available with both tritium and $^{14}$C labels. The main reason is because there is little value for using tritium or $^{14}$C labeled Cystein or Methionine; as a result, these amino acids are not made and sold commercially. With the introduction of radioactive multiplexing techniques, these amino acids will become much more useful especially because they enable triple labeling when $^3$H, $^{14}$C, and $^{35}$S Cystein and Methionine are used for the experiment. Besides the triple labeling experiment, many enzymes can be severely affected when normal hydrogen is replaced with tritium. Because tritium weight three times more than hydrogen, tritium molecular kinetic is much lower. An enzyme reaction that normally involves the exchange of a hydrogen atom will become significantly slower when tritium replaces the hydrogen. As a result, such replacement can significantly alter cellular metabolism, an event that is highly undesirable due to the nature of the experiment. To overcome such shortfall, $^{14}$C labeling can be used to compare with $^{35}$S labeling.

In addition to the amino acids themselves, their metabolic precursors can also be used to perform the same labeling experiment. These metabolic precursors are molecules that can be easily converted and incorporated into protein as Cystein or Methionine while retaining the radioactive label. For labeling to be effective, such precursor encompassed molecules that are unique to Cystein or Methionine biosynthesis pathways, and derivatives of post synthesis. A good example is Cystine, the oxidized form of two Cysteins covalently linked by a sulfide bond. Other slightly modified versions of Cystein or Methionine or larger molecules containing these amino acids as components can also be used as precursors. These precursors are known to those skilled in the art and can vary slightly depending on the biological system used. In addition, when this method becomes more useful, those skilled in the art will be able to apply atomic replacements of nitrogen and oxygen with other radioactive atoms to enable even more multiplexing capability.

Specific Methods of Analysis:

Array—

Protein array is a method that will benefit greatly from this novel approach. An array is used for profiling and analyzing many molecules simultaneously using just minute amount of sample. The current method for detection and quantification of proteins or DNA/RNA on the array use fluorescent dyes, thus the array support only needs to be a sturdy structure that does not fluoresce. This invention provides an array's support that also serves the dual purpose of a screen, which blocks higher proportion of radiation from one particular label but not the others. Depending on the thickness and type of material used, such screen can allow differentially detection and quantification of tritium, carbon-14, sulfur-35, phosphorus-33, phosphorus-32, and other radioactive isotopes from each others. The screening technique is particularly useful for radioactive labeled samples whereby at least most of signal from one label is blocked by the screen while higher percentage of the other signal is allowed to pass making simultaneous detection and quantification of both signals possible.

Figure 4:
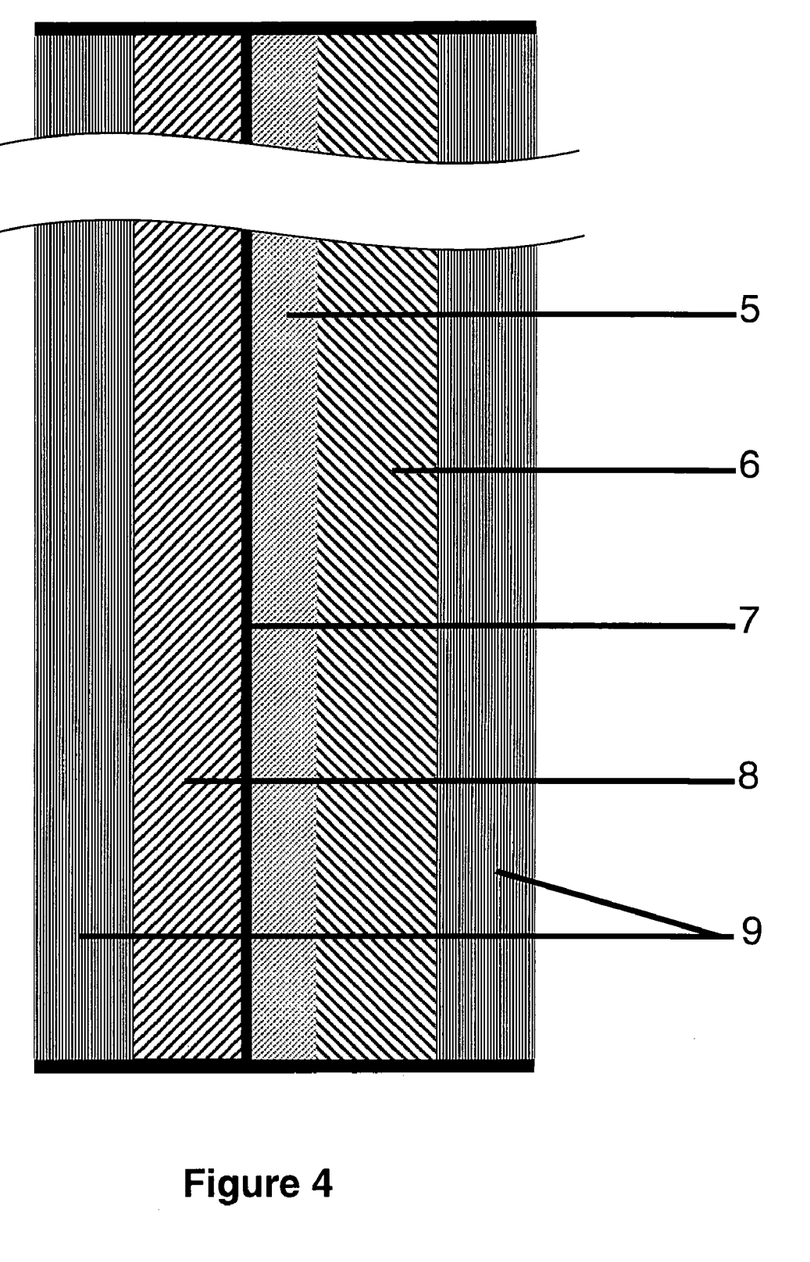
FIG. 4 is a cross-section side view of an array that enables easy detection and quantitative comparison between multiple isotopes.

Another variation of the array support is the inclusion of scintillation material to convert radiation into light for easier detection. With reference to FIG. 4, the array can have a sturdy transparent supporting material 9 such as glass, then a layer of scintillation material 8, then a thin film covering material 7. The thin film will also serve the dual purpose of a blocking screen which will be extremely useful for selectively blocking tritium while allowing a high percentage of $^{14}$C or $^{35}$S signals to pass. On top of the thin film is the activated surface 5 where the antibodies are spotted for capturing and profiling antigens. Once captured, the unscreened radiation from these antigens can be read by placing a second scintillation layer 6 on top of the array and then reading the light emitting as a result of radiation striking scintillation materials. The partially screened radiation can also be read simultaneously from the bottom of the array by reading the light from the embedded scintillation layer. Confocal optical technology allows high resolution reading that can essentially bypass the thickness of the glass layer. To avoid signal crossing over between the top and the bottom screen, the thin film acting as blocking screen also block emitting light. Thicker or denser variation of this screen can also be used to differentially block $^{32}$P and $^{33}$P for DNA arrays or phosphorylation studies.

In yet another variation, a thin film of phosphorescent material is used in place of the first and second scintillation material layers 6, and 8 described above. The phosphorescent material can capture and store the radiation signature to be read back with a properly tuned laser. To read the array, the phosphorescent material is erased by photo-bleaching and then the array is also exposed to another phosphorescent screen "cover slip" on top of the array for equal amount of time before both screens are read.

DNA arrays will also benefit where higher detection sensitivity is needed. Low abundance DNA or RNA can be detected more easily. Even direct detection is possible eliminating the extra amplification steps such as PCR. Other detections for things that cannot be amplified such as DNA modification are also possible. In addition, pre-purification or other enrichment methods can be used prior to array analysis. These methods can range from eliminating certain high abundant DNA/RNA to specifically trapping certain types of DNA/RNA.

Tandem/Multidimensional Chromatography for Proteomic Analysis—

Chromatography methods have not been able to replaced 2-D gel electrophoresis probably due to the lack of a multiplexing approach. Unlike electrophoresis where sample can be compared side by side or multiplexed on the same gel, chromatography of two samples usually have to be done sequentially for comparison. One type of chromatography can separate samples into fractions which can later be used to separate further by another type of chromatography. It is unlikely that the same sample run back to back on many sequential types of chromatography would yield exactly the same set of fractions. Therefore, the method has not been popular for comparing samples. However, with our labeling and detection method, two samples can be mixed together to be co-separated by sequential chromatography. Since the molecules in both samples possess the identical structure and chemistries (from metabolic labeling or covalent linkage with chemically similar tags), the molecules are separated equally regardless of which sample they come from. A radiation detector can monitor the proportion of the isotopes in real-time through a flow cell or small aliquots from fractions can be removed and counted by scintillation counting. Samples labeled with $^3$H and $^{14}$C, or $^{32}$P and $^{33}$P can readily be distinguished by existing scintillation counter. Alternatively, radiation of aliquots from the same fraction can be determined before and after a decay period to allow differential quantification especially for $^{14}$C and $^{35}$S.

Immunoprecipitation:

This is also one of the methods of analysis that will benefit greatly with the multiplexing technique. Current immunoprecipitation experiments involve multiple samples treated in similar manners in parallel. Many sequential steps such as incubating with samples and washing can introduce variation. Sometimes, the amounts of capturing agents recovered also vary because some are inadvertently washed away. Having multiple samples in one run ensure that these samples are always treated equally enabling true comparison.

With the increase in reliability, there can also be other methods similar to immunoprecipitation used to compare any particular molecules between samples. For example, an immobilized DNA sequence can be used to capture labeled RNA from two samples for comparison. Then optionally the captured molecules can be separated later for further analysis if necessary. An obvious advantage of this method is to replace the labor intensive Northern blotting method.

Labeling—

In addition to metabolic incorporation of amino acids, nucleotides or other precursors that are made with one or more atoms replaced with radioactive isotopes, other bioconjugation and molecular replacement methods can also be used. A well-known method is iodination using $^{125}$I to modify Tyrosines. Other coupling methods that add a group of molecules can also be used. These methods use NHS ester, cyanogen bromide, bis-oxirane (epoxides), carbonyldiimidazole, sulfonyl chloride, periodate, fluoromethyl pyridinium sulfonate, glutaraldehyde, acetaldehyde, and formaldehyde . . . etc to create covalent linkage A gentle way to label protein with at least one phosphorylation site is to use a kinase to add a phosphate group with $^{32}$P or $^{33}$P. Protein with known phosphorylation sites can be phosphorylated with specific kinase. The reaction can be used to label protein or to determine the amount of existing phosphorylation in these proteins by quantifying the amount of available phosphorylation sites.

Methods of Detection—

Differential detection is made possible by using a blocking screen that can selectively block higher proportion of radiation from one isotope than from another isotope. A layer of saran wrap can block >95% or radiation from $^3$H, while only blocks ~50% of radiation from $^{14}$C or $^{35}$S. The same layer of saran wrap blocks <40% or $^{33}$P's and <10% or $^{32}$P's radiation. Similarly, an X-ray film can block >95% of radiation from $^3$H, $^{14}$C, $^{35}$S, or $^{33}$P while blocking <30% of radiation from $^{32}$P. This differential blocking efficiency allows quantification of radiation from individual isotope from a mixture using the following procedure:

1. Detect and quantify radiation from two single isotopes say $^{32}$P and $^{33}$P with and without the blocking screen,
2. Use radiation quantity read for 100% $^{32}$P and 100% $^{33}$P without the blocking screen to calculate what the detectable radiation for different percentage mixture of $^{32}$P and $^{33}$P would be,
3. Use radiation quantity read for 100% $^{32}$P and 100% $^{33}$P with the blocking screen to calculate what the radiation for different percentage mixture of $^{32}$P and $^{33}$P would be,
4. Take the predicted quantity of radiation with blocking screen and divide it by the predicted quantity of radiation without blocking screen of the same percentage mixture to obtain the ratio of radiation that can pass through the blocking screen at that particular mixing percentage.
5. Use the ratio of radiation passing through the blocking screen to determine the mixture of $^{32}$P and $^{33}$P isotopes from experimental data.

In the event the ratios vary slightly at different radiation intensity—an event most likely due to peculiarity of the detection system, then different ratios at different radiation intensity from different exposure durations can be determined and used as reference. This can be accomplished simply by reading different amount of each isotope with and without the blocking screen for various durations and then make the necessary calculation.

Besides using a selective blocking screen to block radiation toward a phosphostorage screen, scintillation material, Geiger tubes or other radiation detectors; scintillation spectra can also be used to differentiate and quantify the proportion of two or more isotopes. Tritium emits relatively weak radiation thus generate a spectrum of light with significant difference from spectra generated by $^{14}$C or $^{35}$S. Other isotopes' spectra also are significantly different from each other such as spectra from $^{33}$P and $^{32}$P. The spectra of single isotope can be stored in the reading instrument to allow calculation of the percentage of individual isotope in the mixture by interpolation. Alternatively, spectra of different percentage mixture of isotopes can be stored as standards to compare to spectra of samples to deduce the correct percentage mixture with fewer interpolation needed and higher accuracy.

Scintillation materials and blocking screens can also be combined to make detection of different isotopes possible. Scintillation materials can be coated with different thickness of "blocking screens" so that the radiation that strikes the scintillation materials is selectively blocked. The coating materials can be of various transparent colors so that different signals from different thickness beads can be differentiated. Alternatively, different scintillation materials can be made to emit light within different spectra to be used in different beads.

Scintillation materials and spectral analyzer can also be combined for differential quantification of radiation with different level of energy on flat surface. A gel can be dried onto a scintillation support and then different band-pass filters are used for selective detection of light from just a portion of the spectrum at a time.

In addition to using differences in radiation energy between isotopes to selectively quantify them in a mixture, the differences in half-life can also be used. Mixture of isotopes such as $^{14}C$ and $^{35}S$, or $^{32}P$ and $^{33}P$ can be quantified by reading radiation from one set of aliquots first, while storing a duplicate set of aliquots for decaying to be read later on. The pre-decay and post-decay amounts of radiation are used in combination with the isotopes' half-life to determine the amount of radiation unique to each isotope.

While using radioactive isotopes provides a rapid way to detect and quantified multiplexed samples for rapid quantitative comparison, most samples of interest also require identification by mass spectrometry at least initially. Labeling with different radioactive isotopes produces different mass of the same molecules thus results in distinct peaks in a mass spectrum. Such quality can also be exploited to make quantitative comparison especially to reconfirm previous comparison made with other methods.

Improvements:

Resolution:

A further improvement method for reading arrays or gels that can increase the resolution of the radiation read is the use of a magnetic field to redirect radiant electrons. Beta radiation is essentially electrons or positrons traveling at high velocity. By applying a magnetic field perpendicular to the array, any electrons or positrons not traveling in parallel with the magnetic field will experience a force and be redirected. When electrons mostly travel perpendicular to the array to strike detector or storage screen, better resolution is achieved. This improvement is especially important when multiple layers of screens are used to detect radiation placing them increasingly farther away from the source.

The above description provides a methodology for which a broad spectrum of particular analysis may apply. Accordingly, the following examples are provided to further enhance the users understanding of the invention but in no way are intended to limit the particular application of the method described above.

EXAMPLES

Example 1

Biomarker Discovery and High-Throughput Assay Development

Because of the limited antibodies availability, biomarkers must first be discovered and then antibodies are made against them to build useful antibody arrays for high throughput screening. Current methods use 2-D gel electrophoresis to separate proteins. This example presents an alternative to 2-D gel electrophoresis.

Samples from two sources such as drug-treated and vehicle treated cells are used to look for biomarkers. These samples are prepared so that one is labeled with $^3H$ while the other is labeled with $^{14}C$ by chemically similar labels or by metabolic incorporation and then mixed together for analysis. A small aliquot is counted on scintillation counter capable of distinguishing between $^3H$ and $^{14}C$ to establish the ratio of samples mixture. The mixture is then separated by tandem chromatography. The fractions resulting from one type of chromatography are further separated by another form of chromatography. Every fraction produced is monitored for $^3H/^{14}C$ ratio to select for fractions with significant ratio deviation. These fractions of interest can be analyzed further by SDS-PAGE and applied to the two screen system to quantify $^3H/^{14}C$ ratio. The bands showing significant ratio difference are cut out for identification by mass spectrometry. During mass spectrometry analysis, the mass difference between molecules labeled with different isotopes will also become apparent. For instance, labeling with a methyl group using $^{14}C$ increase the molecular mass by 2 atomic mass units (amu) while labeling with a methyl group containing all three tritium increase the molecular mass by 6 amu. The result is that a $^{14}C$-labeled molecule is 4 amu lighter than a tritium-labeled molecule for every methyl group used. This difference allows the operator to tell whether the correct proteins are being examined and also serves to reconfirm the previous quantification results.

Antibodies are made against the identified proteins or partial protein sequences resulting from mass spectrometry analyses. These antibodies are used to make antibody arrays to rapidly screen for the same biomarker changes in micro format. The array is exposed to the same mixture from original samples to validate their effectiveness in identifying the biomarkers whose changes are originally found by other methods. Once validated, the arrays are ready for high-throughput screening use.

Example 2

Post-Translational Modification Studies

Protein Phosphorylation Study

Post-translational modifications of proteins are very important regulatory mechanism in eukaryotic organisms. One such important modification is phosphorylation: a phosphate added to an enzyme or receptor can turn it on or off depending on the type of enzyme or receptor. Thus a system that enables the comparison of protein phosphorylation with high degree of sensitivity can be a very powerful tool for research and diagnostic use. A dual labeling system using chemically similar labeling agents that comprises either $^{32}P$ or $^{33}P$ is used to determine the degree of phosphorylation in two set of cells or cells undergoing two different treatments.

Cellular drug response can be studied as followed: (1) Cells are grown equally in two culture dishes. Prior to labeling, the cells are starved of phosphate by washing and replacing growth media with phosphate-deficient media for 1 hour. (2) Labeling media are added wherein one contains $^{32}P$ phosphates while the other contains $^{33}P$ phosphates. At the same time one set is (or had been) treated with drug while the other is treated with vehicles (any solvent used to carry the drug) or another drug for efficacy comparison. (3) After a predetermined amount of treatment time, radioactive media is washed away and the cells are harvested and lysed in RIPA buffer with phosphatase inhibitors such as NaF and okadaic acid. The cell lysates are mixed together and subjected to different analyses as described below.

Electrophoresis—

SDS-PAGE and 2-D gel electrophoresis are performed to separate the different proteins for analysis. The gels are then fixed in 10% acetic acid and dry on gel drier. Each dried gels is exposed to special 2-layer phosphorescent imaging storage screen comprising of one thin screen made of phosphorescent and backing material just enough so that most of the $^{33}$P signal cannot pass through. The other screen is also made of the identical phosphorescent material but placed on much better backing plate. The first screen was designed to capture both radiation signals from $^{32}$P and $^{33}$P while allowing much higher proportion of radiation signal from $^{32}$P to pass through to the second screen. Since $^{33}$P signal is relatively weak, the first screen can be thin enough so that the signal picked up on the second screen is not significantly more diffused. Additionally, a strong magnetic field can be used to minimize such diffusion. Then the screens are read using phospho-imaging reader and the result interpreted by specialized software. Using known internal standards for calibration such as signal unique to just $^{33}$P or $^{32}$P, then the same signals from sample mixtures are calculated and compared for bands or spots of proteins of interest. From these calculations, the relative amount of phosphorylation for each protein between samples is calculated. These differences can assess the relative drug effectiveness.

Immuno-Precipitation—

The mixed cell lysate is subjected to immuno-precipitation to study the phosphorylation and its effect on protein interaction. Lysate is precleared with protein G coupled to sepharose beads. Then appropriate antibody is added and incubated for 2 hours followed by the addition of protein G sepharose beads for an additional hour. Beads are collected by centrifugation, washed for at least three times to remove non-specific interaction, and then subject to SDS-PAGE analysis. The gel is fixed, dried marked with control markers, and then exposed to the two-layer phosphorescent imaging screen system designed for $^{32}$P and $^{33}$P. The screens are read and the bands of interest are quantified and normalized with control markers enabling quantitative comparison between the two samples. Proteins co-labeled with $^{3}$H and $^{14}$C for interaction studies can also be differentiated and quantified especially after a decay period.

Tandem/Multidimensional Chromatography

As described earlier, different methods of chromatography can be used to look for proteins with variation in phosphorylation when apply to this experiment. The isolated proteins can be identified by existing methods including mass spectrometry.

Determination of the Degree of Protein Phosphorylation in Clinical Samples:

A variation of the above method is used to compare the degree of phosphorylation for one or a plurality of proteins between two clinical samples. The sample are fractionated to some degree of purity suitable for the experiment before one of the sample is subjected to kinase phosphorylation using $^{32}$P ATP while the other sample with $^{33}$P ATP. The kinases will add phosphate groups to phosphorylation sites that do not already have phosphates. Because there are many kinases and each of them will specifically phosphorylate different sites, this method can target specific protein or family of proteins. After kinases reactions, the resulting proteins are mixed together for various types of analyses as outlined above.

Tritium and $^{14}$C-Labeling for Glycosylation Study

Other posttranslational modification such as glycosylation can also be studied using $^{3}$H and $^{14}$C substrates. The detection using a two-layer phosphorescent screen can be difficult since the first screen should be as thin as a saran wrap for $^{14}$C signal to go through and construction of such screen is so prone to damage. To solve this technical problem, the gel destined for analysis is dried onto a thin support film that would block most of the $^{3}$H signal but allow a good proportion of $^{14}$C signal to pass. The gel is then exposed to two phosphorescent screens: one on the gel side and one on the thin film backing side. A less convenient method is to expose the gel to one screen, and then expose again to a similar screen with a built-in tritium blocking screen for the same amount of time. The signals are then quantified accordingly. In addition to quantification done by phosphor-imager, the dots or bands of interest can also be cut out for scintillation counting, or mass spectrometry analysis. Scintillation counter technology is advanced enough to enable the instrument to distinguish the difference between emissions resulting from $^{3}$H versus that resulting from $^{14}$C. While the main quantification method for radioactivity presented here uses phosphoimaging screen and scintillation counting, other methods, variations and combinations of existing methods can be used and are apparent to those skilled in the art.

Example 3

Genomic/RNA Expression Studies

For tissue samples where RNA is readily extracted, the RNA can be labeled with either $^{32}$P or $^{33}$P at their end terminals and then applied to a complementary DNA array. The array is then exposed to the two-screen phosphorescent imaging system so signals specific to either $^{32}$P or $^{33}$P could be quantified and compared after normalized with internal controls' signals. Alternatively, total signals can be quantified before and after a few days and used to calculate signal unique to $^{32}$P or $^{33}$P. The half-life of $^{32}$P is shorter than that of $^{33}$P (14.3 days compared to 25.3 days) thus makes the calculation possible. For higher sensitivity in smaller tissue sample, a Reverse Transcriptase reaction can be performed with either $^{32}$P or $^{33}$P labeled poly dT or labeled nucleotides. The poly dT is hybridized to the poly A tail of mRNA and reverse transcriptase synthesizes the rest of the complementary sequence to form a single stranded cDNA. The RNA is then digested away by RNAse and the cDNA is applied to an array for analysis.

In addition to comparing mRNA expression for the same genes between the two tissue samples, these procedures can also compare the expression level of different genes in the same tissue because each RNA molecule is labeled with the same amount of radioactivity (except when cDNA is synthesized with labeled nucleotides. For further improvement in sensitivity, radioactive nucleotides i.e. [$^{32}$P/$^{3}$P]-dATPs are used for the synthesis step so more labels are incorporated into each molecule. For this method, $^{35}$S nucleotides can also be used in place of $^{33}$P nucleotides. When using difference half-life to differentially quantify the isotopes, $^{35}$S is also superior with half-life of 87.2 days compared to $^{33}$P's half-life of 25.3 days while comparing with $^{32}$P's half-life of 14.3 days and is also much safer to work with.

Example 4

DNA Methylation Study

Variation in DNA methylation has been found in many forms of cancers. The detection of abnormal DNA methylation thus can be used to detect and diagnose cancers or cancer onsets. The identification of genes that are commonly methylated in many cancers can also help elucidate certain function for these genes' products. For instance, when onco-genes are heavily methylated, cell division is left unchecked leading to neoplastic conditions. DNA from a cell type of a patient sample and that from a known healthy donor sample is extracted for the purpose of comparing the degree of methylation. The DNA from both samples is treated with methyl transferase (the enzyme that methylates DNA). In one sample Adenosyl-L-Methionine, S-[methyl-$^{14}$C] is used while in the other sample Adenosyl-L-Methionine, S-[methyl-$^{3}$H] is used as methyl donor. The methylation reaction is allowed to progress to completion for the purpose of methylating all remaining sites that has not already have a methyl group. Then both DNA samples are mixed together and subjected to restriction digest. The DNA fragments are then profiled on DNA array for quantitative comparison of $^{3}$H and $^{14}$C labels. The result is interpreted to indicate any abnormal increase or decrease in DNA methylation for any particular genes in patient compared to healthy donor. For more reliability in controlling the methylation reaction between two samples, exogenous DNA with known methylation sites and different degree of methylation is added as controls. The array is also redesigned to include aptamers to capture and profile these exogenous DNA.

Example 5

Rapid Point-of-Care Clinical Diagnostic

After biomarkers for certain conditions such as onset of cancers or host responses to common infection vs. those caused by biological warfare agents are identified, diagnostic arrays can be made to rapidly diagnose these conditions. The more biomarkers used for these diagnoses, the more reliable the assays are. To enable rapid diagnostic, the arrays are made with embedded scintillation screens to enable direct detection. A thin film separating the scintillation material from the binding agents will serve to block higher proportion of weaker isotopes. Alternatively, one single layer of scintillation material can be used along with different spectral filters to enable differential quantification of light resulting from radiation of different energy.

Clinical samples from patients and healthy volunteers (or samples from the same patient taken and stored when healthy) are used for making comparisons. The samples are labeled with different isotopes and then mixed together for competitive binding to the same array. After binding, radiation from different isotopes is rapidly quantified using scintillation material to convert such radiation into light and sensors to detect and count the light emission. Quantitative comparison is possible using captured housekeeping proteins or genes as comparison standard. The relative amount of biomarkers between normal and patient's sample is used as the basis for making diagnosis.

Other uses for the present invention are not discussed thoroughly in this disclosure; however, are still encompassed by the present invention. For example, the disclosed methods may be, of course, utilized in proteomics studies, genomics studies, metabolomics studies, glycomics studies, and in vitro diagnostic applications. In addition to using the invention to make abundance comparison of similar molecules or molecular characteristics, using known amount to quantify an unknown amount of similar molecules is also possible. Specific details with regard to these particular uses for the present invention are known and understood by one skilled in the art.

It should be clear that the methods disclosed in this invention may be coupled with various other studies, or used with many other means of analysis. While the description emphasizes studies of proteins, DNA and RNA; other molecules can be studied with variations of this method.

What is claimed is:

1. A method of analysis comprising the steps of:
   (a) labeling molecules in a first sample with a first radioactive isotope;
   (b) labeling molecules in a second sample with a second radioactive isotope that is different from said first radioactive isotope;
   (c) mixing said first sample and said second sample into a mixture;
   (d) separating said mixture into a plurality of groups of molecules; and,
   (e) using the difference in half-life between said first radioactive isotope and said second radioactive isotope as a means to selectively quantify each isotope in each group of molecules.

2. A method of analysis comprising the steps of:
   (a) labeling molecules in a first sample with a first radioactive isotope;
   (b) labeling molecules in a second sample with a second radioactive isotope that is different from said first radioactive isotope;
   (c) mixing said first sample and said second sample into a mixture;
   (d) separating said mixture into a plurality of groups of molecules; and,
   (e) selectively quantifying each isotope from each group of molecules wherein a screen is used to selectively block a higher proportion of radiation from one isotope.

3. The method of claim 1 or claim 2 further comprising the steps of:
   (a) calculating the ratio of said first radioactive isotope to said second radioactive isotope in each group of molecules; and,
   (b) comparing the ratios of radioactive isotopes between the groups of molecules whereby a group of molecules with a deviated ratio of radioactive isotopes can be identified.

4. The method of claim 3 further comprising a step of: isolating at least one molecule responsible for said deviated ratio of radioactive isotopes from said group of molecules with a deviated ratio of radioactive isotopes.

5. The method of claim 4 further comprising a step of: identifying the isolated molecule.

6. A method of isolating a difference between two samples comprising the steps of:
   (a) labeling molecules in a first sample with a first radioactive isotope;
   (b) labeling molecules in a second sample with a second radioactive isotope that is different from said first radioactive isotope;
   (c) mixing said first sample and said second sample into a mixture;
   (d) separating said mixture into a plurality of fractions;
   (e) quantifying a ratio of radioactive isotopes for each fraction; and, (f) comparing the ratios of radioactive isotopes among all fractions whereby at least one fraction with deviated ratio of radioactive isotopes is identified as a result said difference is isolated.

7. The method of claim 6 further comprising a step of: isolating at least one molecule responsible for causing said deviated ratio of radioactive isotopes from said fraction with deviated ratio of radioactive isotopes.

8. The method of claim 7 further comprising a step of: identifying the isolated molecule.

9. The method of claim 6 further comprising a step of: separating a fraction with normal ratio of radioactive isotopes into a plurality of sub-fractions.

10. The method of claim 9 further comprising a step of: comparing the ratios of radioactive isotopes among all sub-fractions whereby at least one sub-fraction with deviated ratio of radioactive isotopes is identified.

11. The method of claim 9 further comprising a step of: comparing ratios of radioactive isotopes among all sub fractions and said all fractions whereby a sub-fraction with deviated ratio of radioactive isotopes can be identified.

12. The method of claim 10 or claim 11 further comprising a step of:
isolating at least one molecule responsible for causing said deviated ratio of radioactive isotopes in said sub-fraction with deviated ratio of radioactive isotopes.

13. The method of claim 12 further comprising a step of: identifying the isolated molecule.

14. A method for finding a difference between two protein samples comprising the steps of:
(a) labeling protein molecules in each sample with a unique radioactive isotope whereby one isotope is used per sample;
(b) mixing the labeled protein molecules from said two samples together into a mixture;
(c) contacting said mixture with an array;
(d) measuring a ratio of radioactive isotopes at each spot on said array; and,
(e) comparing the ratios of radioactive isotopes among a plurality of spots on said array whereby a spot with deviated ratio of radioactive isotopes can be identified.

15. The method of claim 14 wherein a screen is used as a means to enable the measurement of a ratio of radioactive isotopes at each spot on said array.

16. The method of claim 14 wherein the difference in half-life between the two isotopes is used as a means to enable the measurement of a ratio of said two isotopes at each spot on said array.

17. The method of claims 14 further comprising a step of: applying a magnetic field to said array to improve the resolution of radiation detected.

* * * * *